United States Patent [19]

Farin

[11] Patent Number: 4,969,885
[45] Date of Patent: Nov. 13, 1990

[54] HIGH FREQUENCY SURGERY DEVICE FOR CUTTING AND/OR COAGULATING BIOLOGIC TISSUE

[75] Inventor: Günter Farin, Tübingen, Fed. Rep. of Germany

[73] Assignee: Erbe Elektromedizin GmbH, Tübingen, Fed. Rep. of Germany

[21] Appl. No.: 477,117

[22] Filed: Feb. 7, 1990

Related U.S. Application Data

[63] Continuation of Ser. No. 272,504, Nov. 16, 1988, abandoned.

[30] Foreign Application Priority Data

Nov. 17, 1987 [EP] European Pat. Off. ......... 87116954.6

[51] Int. Cl.$^5$ .............................................. A61B 17/39
[52] U.S. Cl. ........................................ 606/38; 128/908
[58] Field of Search ..................... 606/37–40; 128/908

[56] References Cited

U.S. PATENT DOCUMENTS

| | | | |
|---|---|---|---|
| 3,601,126 | 8/1971 | Estes | 128/303.14 |
| 3,897,787 | 8/1975 | Ikuno et al. | 128/303.14 |
| 4,092,986 | 6/1978 | Schneiderman . | |
| 4,102,341 | 7/1978 | Ikuno et al. | 128/303.14 |
| 4,114,623 | 9/1978 | Meinke et al. | 128/303.14 |
| 4,126,137 | 11/1978 | Archibald | 128/303.14 |
| 4,271,837 | 6/1981 | Schuler | 128/303.14 |
| 4,281,373 | 7/1981 | Mabille | 128/303.14 |
| 4,658,819 | 4/1987 | Harris et al. | 128/303.13 |
| 4,862,889 | 9/1989 | Feucht | 606/38 |

FOREIGN PATENT DOCUMENTS

| | | |
|---|---|---|
| 2801833 | 4/1979 | Fed. Rep. of Germany . |
| 3531576 | 5/1986 | Fed. Rep. of Germany . |
| 3623688 | 1/1987 | Fed. Rep. of Germany . |
| 3600990 | 7/1987 | Fed. Rep. of Germany | 128/303.14 |

OTHER PUBLICATIONS

DIN/IEC 601 Part 2—2, Sep. 1984.
"Possibilities and Problems of the Standardization of High Frequency Power", in the collection Hochfrequenzdiathermie in der Endoskope, published by G. Lux and K. Semm, of Springer-Verlag, Berlin, Heidelberg, 1987.
Revue Generale De L'Electricite, No. 10, Oct., 1981, pp. 731–737.

Primary Examiner—Lee S. Cohen
Attorney, Agent, or Firm—Frishauf, Holtz, Goodman and Woodward

[57] ABSTRACT

A high frequency AC electro-surgery apparatus is equipped with an automatic regulation loop for controlling the output voltage ($U_a$) rather than the output power. An electrically isolating coupling in the form of an isolation transformer (5) is followed by a voltage converter (6) to provide DC voltage signal (a) proportional to a measure of the high frequency AC output voltage ($U_a$). The DC voltage signal (a) is supplied to a regulating amplifier (7) to which a reference voltage signal (b) is supplied by a reference voltage source (8), to produce an output signal (c) that is furnished to the control input of an electronically controlled power supply (16). The latter controls the operating voltage ($U_b$) for the amplifier (2) of the high frequency AC generator in such a manner that the output AC voltage ($U_a$) at the output terminals (10, 11) corresponds to a desired value set by the reference voltage signal (b).

16 Claims, 4 Drawing Sheets

HIGH FREQUENCY SURGERY DEVICE FOR CUTTING AND/OR COAGULATING BIOLOGIC TISSUE

This application is a Continuation of application Ser. No. 07/272,504, filed Nov. 16, 1988, now abandoned.

This invention concerns surgical apparatus for cutting or coagulating biologic tissues by means of high frequency electric alternating current.

Devices of this general kind have been known for over fifty years and for many years already they have become part of the equipment of surgery premises of a wide variety of surgical specialty practices.

The properties of high frequency surgery equipment as well as the requirements based on such equipment are defined and established in national and international standards, for example in DIN/IEC 601, Part 2- 2, published in Germany in September, 1984.

Essential components of all high frequency surgery devices are high frequency generators which generate the high frequency electric alternating current required for cutting and/or coagulating living tissue. In order to avoid electrical stimulation of nerves and muscles, the frequency of the alternating current should be at least 300 kHz. The nominal output power of high frequency surgical equipment, for reasons of safety of the patient and of the operators, may not exceed 400 watts averaged over one second.

According to the surgical specialty and the particular individual application, more or less high power is necessary for cutting and/or coagulating. For this reason high frequency electrode surgery apparatus is equipped with adjusting means for the output power. According to DIN/IEC 601, part 2- 2, high frequency electro-surgery apparatus must be equipped with adjusting elements by which the output power can be dropped to not more than 5% of the nominal output power or to 10 watts, whichever is lower.

Since the introduction of high frequency electro-surgery more than fifty years ago it has been recognized that the power which is dissipated in biological tissue by high frequency electro-surgery devices depends upon various parameters. The most important parameters determining power consumption are the idling voltage, sometimes referred to as the open circuit voltage, and the internal resistance of the particular high frequency generator, as well as the electrical resistance of the biological tissue or load resistance. In order to make clear to the operators the dependence of the power supplied from the high frequency electro-surgery apparatus to the load resistance, the manufacturer must include, in the technical description of the apparatus, in accordance with article 6.8.3 DIN/IEC 601, Part 2- 2, diagrams which represent the power output at full power and half power adjustment control of the power setting across a load resistance range from 50 to 2000 ohms. The diagrams must show this for all modes of operation, such as cutting, coagulating and coagulative cutting. Furthermore diagrams must also be supplied which show the power output as a function of the position of the power adjustment control for a given load resistance in the range from 50 to 2000 ohms for the above-mentioned modes of operation.

The above-described diagrams help the operator best when he is selecting a suitable high frequency electro-surgery device for his special application. During its use, especially when the same high frequency electro-surgery device is utilized for various operations, these diagrams do not help the operator at all. The power output that is necessary during cutting or coagulation is not constant, as is often mistakenly assumed, but rather dependent on many different parameters, such for example as depth and speed of cutting, size of the effective contact surface between coagulation electrode and tissue, temperature of the tissue to be coagulated and physical properties of the tissue that is to be cut or to be coagulated. In practice neither the power necessary for any particular cutting and/or coagulation procedure nor the power delivered by the particular high frequency electro-surgery device at any moment of the cutting or coagulation procedure is constant. This circumstance makes the use of high frequency surgery more difficult to the extent that the reproducibility of the cutting and/or coagulation effects, for obtaining constant quality of these effects, is very difficult.

In spite of this complex of problems, more and more high frequency surgery devices have become known for several years which are equipped with digital number indicators showing power levels that do not however refer to the power output of the high frequency surgery equipment at the time, but, at least in most cases, only to the theoretically possible power output when the output is matched to the load. Such an indication is no more and no less useful to the operator, however, than a dimensionless scale at the power adjustment control. For these reasons DIN/IEC 601 Part 2- 2 also prescribes in this respect that the power adjustment for the output power must be equipped with a scale or indicating device which shows the output high frequency power in relative units. In addition, a division of the scale for the output power into 10 main intervals is also recommended there.

The problematic aspects of output power of high frequency electro-surgery apparatus is thoroughly described in the article by D. Farin: "Possibilities and Problems of the Standarization of High Frequency Power", in the collection "Hochfrequenzdiathermie in der Endoskope", published by G. Lux and K. Semm, of Springer-Verlag, Berlin, Heidelberg, 1987.

In the case of conventional high frequency electro-surgery devices an optimal fit is almost never obtained between the power delivered by the apparatus and the power required from cut to cut or from coagulation to coagulation. Therefore, in every individual cutting or and/or coagulation process, the quality of the cuts and/or coagulations fluctuates more or less strongly.

An electro-surgery generator is known from German published patent application DE 3531576 A which is said to have solved a few of the above-described problems by regulating the output power of this generator in a more or less extensive range of load resistance, automatically, to a constant value with reference to an adjustable desired output power value. This solution contradicts the practical experience that the power necessary during cutting and/or coagulation procedures is not constant, but dependent upon various parameters already mentioned above.

Out of this consideration of the problems there arises additionally the further problem that it is quite impossible to provide an automatic monitoring of whether the high frequency surgery device delivers more or less power than what is necessary for the particular purpose. That has the consequence in practice that more tissue is thermally damaged than is necessary for the surgery, or else that the desired effect is not obtained. In critical operations, as in the field of operative endoscopy, for example this can lead to grave complications, as the relevant experience shows.

A high frequency surgery apparatus is known from U.S. Pat. No. 4,092,986 in which a feedback circuit from the output to the input of the oscillator is provided in order to hold the selected output voltage at a constant level independent of the load resistance. For this purpose an automatic regulation circuit of a mode of operation which is in itself known is shown, which consists of a generator of which the actual value of the output voltage is furnished by means of a detector and compared with a desired or reference value so that deviations of the actual value from the desired or reference value affect the generator to keep the deviation or error signal at the smallest possible value.

The goal just described is only insufficiently approached by the apparatus described in U.S. Pat. No. 4,092,986, however. The detector which furnishes the actual value of the output voltage consists of a coil which is coupled to the inductive component of the resonance circuit of the oscillator. Proportionality between the output voltage of the generator at the output terminals and the output signal of this detector is only unsatisfactorily available. A voltage drop at a capacitor is in general present in the utilization current circuit, the capacitor serving to block low frequency currents and their possible stimulation effect on the nerves and muscles. This capacitance may not be greater than 5000 pf according to the International Standards IEC 601 Part 2- 2. The voltage drop across this capacitance is not taken into account in U.S. Pat. No. 4,092,986. Such a capacitor, for example, has an equivalent resistance of 63.7 ohms at 500 kHz and 106 ohms at 300 kHz.

Since current strength between a few mA in about 2000 mA are found in cutting and coagulation procedures, there are fluctuations of the output voltage up to about 200 volts. In special applications, in which even greater intensities arise, although only for short times, the output voltage fluctuates correspondingly more. In consequence the desired reproducibility of the cutting and/or coagulation quality is not obtained.

SUMMARY OF THE INVENTION

It is an object of the present invention to constitute high frequency electro-surgery apparatus in such a way that the above explained problems are avoided and in particular it is an object to improve high frequency surgery apparatus in such a way that the above-mentioned parameters which influence the required power for cutting and/or coagulation procedures are taken into account automatically to a great extent, so that the quality of the cuts and of the coagulations becomes independent of these parameters. Furthermore, it is an object of the invention to make possible equipment of high frequency electro-surgery apparatus with indicator devices which reliably show relevant parameters determined by high frequency surgery apparatus which correlate with the quality of the cut and/or of the coagulation and show them to the operator before and during the cutting and or coagulating. A further object is to make possible high frequency electro-surgery apparatus equipped with safety devices which monitor the maintenance of relevant parameter values for the cutting and/or coagulation procedures and signalize deviations from desired values of the these parameters.

Briefly, a voltage converter coupled to the output terminals for the utilization current circuit through an electric isolation barrier provides an output signal $f(U_a)$ to a regulating amplifier to which a reference value signal of a reference value source is supplied. The output of the regulating amplifier is supplied to an amplifier that is contained in the high frequency generator and controls the last mentioned amplifier, in such a way that the operating supply voltage $U_b$ for the last-mentioned amplifier is always of such a size that the output voltage $U_A$ at the output terminals corresponds to a desired value set by the desired value signal. Preferably the electrical isolation is in the form of an isolating transformer or an optical coupler.

The invention proceeds from the recognition that for cutting or coagulating biological tissue by means of high frequency electric alternating current the heretofore necessary more or less fluctating power required from cut to cut, from coagulation to coagulation and during each cutting and/or coagulation process can be neither optimally preset in conventional high frequency surgery apparatus nor delivered optimally for responding to the power requirement existing at each instant during an individual cutting and/or coagulation proceeding.

The above-mentioned problems which result from the discrepancy between the power necessary for cutting and/or coagulating procedures and the power delivered by conventional high frequency surgery devices will be avoided in the use of the high frequency surgical apparatus of the invention because, in this apparatus, not the power but rather the output voltage is set, controlled and indicated as the criterion for cutting and/or coagulation effects. It is required for this purpose, however, that the output voltage of the high frequency surgery device for cutting and/or coagulation procedures can be definitively set and that the preset voltage value will be regulated automatically and sufficiently fast to the predetermined level for all relevant load resistances.

The invention further proceeds from the recognition that a minimum voltage of about 150 $V_{eff}$ is required for cutting biologic tissues by means of high frequency electrical alternating current, in order to reach the electrical field strength that is necessary to ignite and to maintain electric arcs between cutting electrode and tissue. In this connection it is also important to observe that even slight rises of the output voltage above the minimum voltage plainly vary the cut quality, and do so in such a way that the intensity of the electric arc becomes plainly greater and thereby also the degree of coagulation of the cut surfaces, during the cutting. It is important in this connection also that the cut quality is to a great extent independent from the cutting speed and the depth of the cut if the output voltage is held constant.

In coagulation with difficult coagulation electrodes, such as for example surical or plate electrodes, it could be observed that the coagulation procedure and the coagulation quality is to a great extent independent of the contact surface between the particular coagulation electrodes and the biologic tissue if the output voltage is maintained constant. Here again, however, even small changes of the output voltage as a result of the physical or that the power is proportional to the square of the voltage, already produced relatively great changes of the coagulation quality.

The solution provided by the invention to the problem of quality control in electro-surgery is distinguished from the known regulation scheme mentioned above and that the output voltage present at the output terminal is automatically controlled and automatically regulated to an adjustable level by means of the variable reference value signal source. It would be still better to provide the control and automatic stimulation of the electrical voltage directly between the active electrode and the neutral electrode or even between the active electrode and the biological tissue in the neighborhood of the cutting or coagulation procedure or directly at the pulls of bi-polar electrodes.

The invention takes particularly into account the problem that a definitive voltage regulation is possible only when the form of the voltage in terms of its harmonic components and/or anharmonic frequencies remains constant during all relevant operating conditions, since otherwise the ratio of peak value to effective value or of effective value to any specified average value of the voltage would not be constant. The high frequency surgery apparatus of the invention can, for this reason, be further improved by equipping it with a high frequency generator which generates constant voltage waveform independent of all relevant operating conditions, preferably a pure sinusoidal waveform.

The high frequency surgery device of the invention offers not only the advantage of reproducible and constant quality of cutting and/or coagulation procedures, but in addition also the advantage that the output voltage before and during cutting and/or coagulation procedures can be automatically controlled and indicated on an electronic indicating device. Thus, the actual value of the output voltage can be automatically compared with the reference value of the output voltage an optical and/or acoustic signals can be generated as soon as tolerance limits are crossed, with the tolerance limits themselves being selectable either in the design equipment or by the operator in the use of the equipment. With tolerance submits being selectable by the user for the deviation of the actual voltage value from the reference value of the output voltage, and excessive or insufficient voltage can also be made to produce an automatic shutting down of the high frequency generator. The indication of the actual value and/or of the reference value of the output voltage makes possible both a presetting of the output voltage before the apparatus is used for cutting and/or coagulation and also a control of the output voltage during cutting and/or coagulation procedures.

In a further embodiment of the invention high frequency surgery devices can be equipped with reference value signal sources that provide outputs of various reference values. In such cases different cutting and/or coagulation properties can be preprogrammed and can be called out as needed by various push buttons or the like on the electrode handles, by various pedal controls, or for example through keys or push buttons in the front panel of the high frequency surgery device. For such embodiments semi-conductor circuits and microprocessors offer control possibilities that can be implemented with compact and economical auxiliary equipment of known types.

BRIEF DESCRIPTION OF THE DRAWINGS

The invention is further described by way of illustrative examples with reference to the annexed drawings, in which.

DESCRIPTION OF THE ILLUSTRATED EMBODIMENTS

Figure 1:
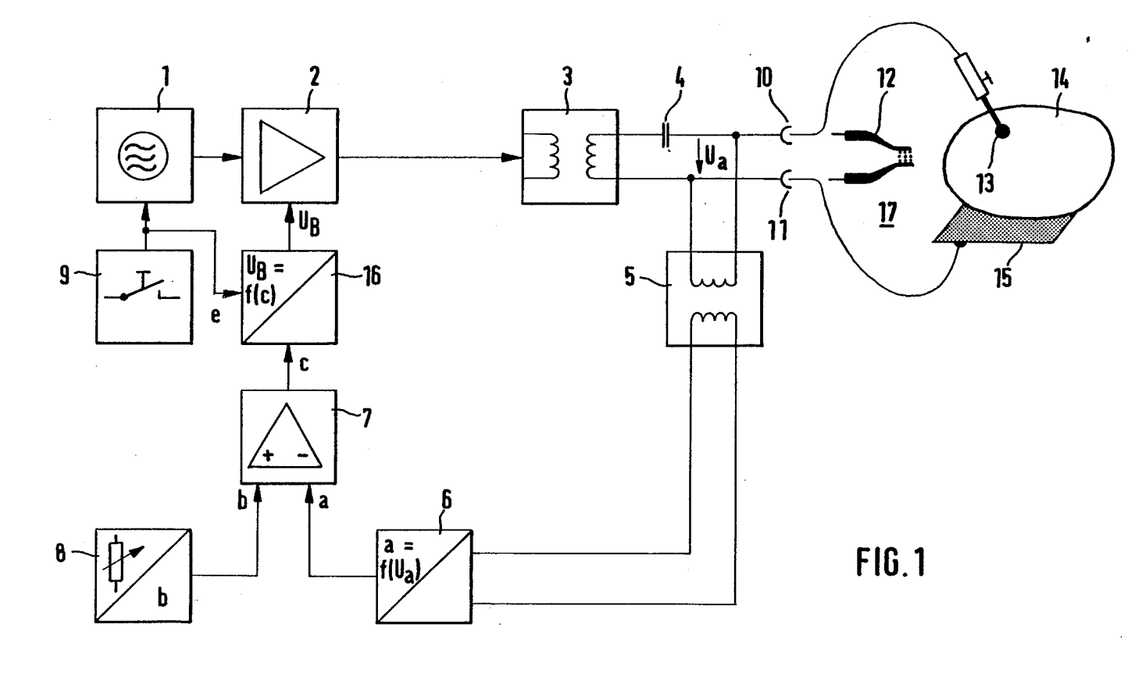
FIG. 1 is a circuit block diagram of an illustrative embodiment of a high frequency electro-surgery device according to the invention.

FIG. 1 shows in a circuit block diagram the basic components of a high frequency electro-surgery device according to the invention. The output voltage $U_a$ which is present at the output bushing terminals 10 and 11 is supplied through an isolating transformer 5 through a voltage converter 6 which delivers and electrical signal $a=f(U_a)$ which is proportional to the output voltage $U_a$. If the output voltage of the output terminals 10 and 11 is not purely sinusoidal, but rather has a content, which is not negligible, of harmonic or anharmonic overtones of the fundamental frequency and/or if the output voltage $U_a$ is modulated in amplitude, while these deviations from fairly sinusoidal waveshape, moreover, are not constant, but dependent upon operating conditions, then it must be checked whether the electrical signal $a=f(U_a)$ would be proportional to the peak value, to the effective value or an average value of the output voltage $U_a$. The voltage converter 6 must be designed or selected in accordance with the foregoing, namely, whether the output electrical signal is to be proportional to the peak value, the effective value or to an average value of the alternating output voltage $U_a$. Suitable voltage converters which deliver the signal $a=f(U_a)$ proportional either to the peak value, the effective value or an average value of the output voltage $U_a$ are known in the art and for that reason do not need to be described in further detail here.

The isolating transformer 5 is necessary in order to assure a sufficiently long electrical isolation path between the utilization current circuit 17 and the internal operating voltage of the high frequency surgery device on the one hand and ground potential on the other hand. This necessary electrical isolation can, however, also be provided with other kinds of components, as for example by means of optical couplers in which, for example, a glow lamp connected to the output voltage $U_a$ produces light which falls on a photosensitive element, a phototransistor or a photosensitive resistance so that fluctuations in brilliance of the glow lamp resulting from fluctuations of the output voltage $U_a$ result in proportional electrical signals at the outputs of the photosensitive element or detector, phototransistor or photosensitive resistance. That type of voltage conversion with electrical isolation between input and output would provide an electrical signal proportional to the effective value of $U_a$.

The electrical signal $a=f(U_a)$ is supplied to a regulating amplifier 7, for example a differential amplifier, to which an electrical signal d is also supplied which determines the desired value of the output voltage $U_a$. The signal b is provided by reference value generator or source 8, which can be constituted to provide the signal of constant value which is adjustable to a desired value or it may be designed to provide the signal b modulated in amplitude at any desired level. According to how great or small the time constant of regulation of the regulation loop as a whole, the output voltage $U_a$ follows the reference value signal b more or less proportionately. The output signal $c = f(b-a)$ with the regulating amplifier 7 can be supplied, for example to the amplifier 2 where it controls the amplification factor thereof, or preferably to an electronically controlled power supply unit 16 which supplies operating voltage for the amplifier 2, in which case it controls the operating voltage of the amplifier 2 in such a way that the output voltage $U_a$ is proportional to the signal b with the reference value signal source 8.

The feedback coupling of a signal $a = f(U_a)$ which is proportional to the output voltage $U_a$ at the output terminals 10 and 11 of the high frequency surgery device for the purpose of automatic regulation of that output voltage to a desired value determined by the reference value signal b is important because as the electrical current in the application current circuit 17 both in the case of coagulation and in the case of cutting procedures fluctuates very strongly more or less large voltage drops occur, for example, at the capacitor 4 as already mentioned above.

For completeness there are also shown in FIG. 1 an oscillator 1 which is activated by a key or a pedal 9, a schematically illustrated biologic tissue 14, an active electrode 13 and a neutral electrode 15 and also as an available substitute for those electrodes, a bipolar electrode 12.

Conventional high frequency electro-surgery devices are as a rule equipped with high frequency generators which have final stage amplifiers that operate in the switching mode, in view of obtaining the highest possible efficiency, with the result that the waveform of the output voltage $U_a$ deviates more or less from a pure sinusoidal waveshape. This deviation from pure sinusoidal form is also dependent on the operating conditions of the high frequency surgery device, the definition of proportionality of the electral signal $a = f(U_a)$ becomes problematic to the extent that the ratio of the peak voltage of $U_a$ to the effective value or to an average of $U_a$ is not constant. Since the shape of $U_a$ is dependent, for example, on load resistance in conventional high frequency high frequency electro-surgery devices, it needs to be defined how the output voltage $U_a$ should be evaluated on the one hand for coagulation procedures, in which the coagulation electrode which pushes the tissues to be coagulated during the entire procedure and, on the other hand, for cutting procedures, in which the cutting electrode does not touch the biologic tissue 14 during the cutting procedure, and instead current flows through electric arcs between cutting electrode 13 and biologic tissue 14. In coagulation procedures, in which the current flows directly without arc formation from the coagulation electrode 13 into the biologic tissue 14 which is to be coagulated, so that as a result only the effective value of the output voltage $U_a$ is significant, the signal $a = f(U_a)$ could be proportional to the effective value of the output voltage $U_a$. For such operations photoelectric voltage converters are particularly suitable as already mentioned above.

The dependence of proportionality of the electrical signals a on the waveform of the output voltage $U_a$ can be avoided by the use of a high frequency generator which delivers a sinusoidal output voltage $U_a$ to the output terminals 10 and 11 under all relevant operating conditions, the output thus being free of harmonic and anharmonic frequencies related to the fundamental frequency. An advantageous embodiment of the high frequency electro-surgery device of the invention accordingly provides a high frequency generator which generates so far as possible only the fundamental frequency, thus, so far as possible, no harmonic or anharmonic frequencies related to the fundamental frequency.

Figure 2:
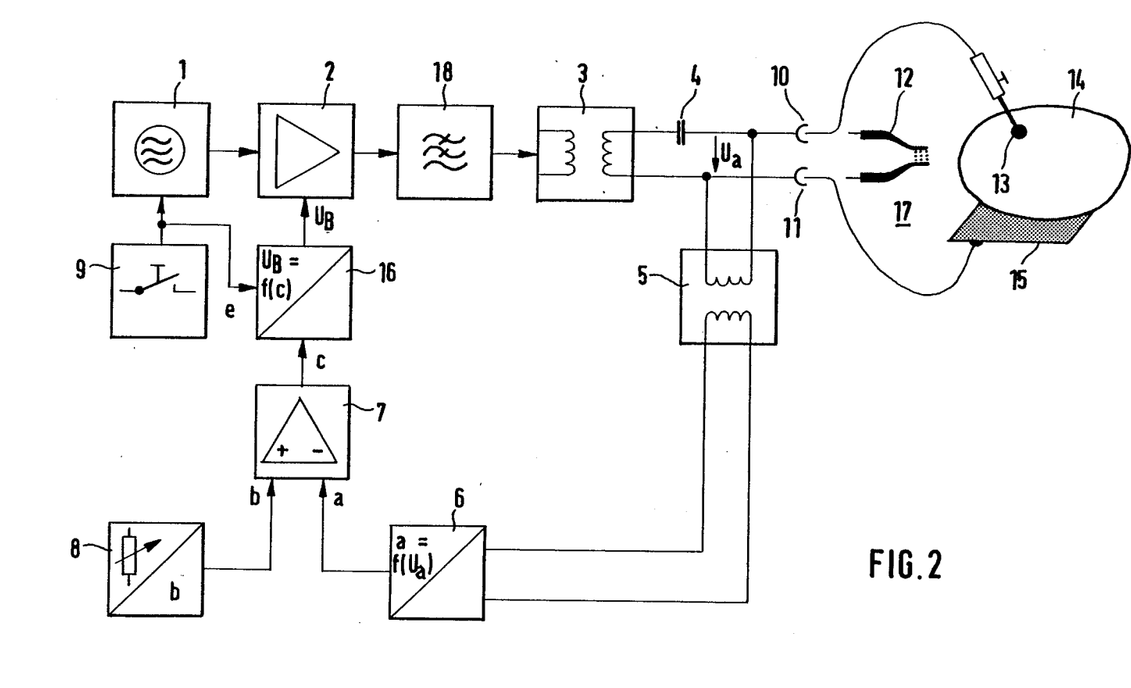
FIG. 2 is a circuit block diagram of a second and improved embodiment of a high frequency electro-surgery apparatus according to the invention.

FIG. 2 shows an illustrative embodiment of high frequency electro-surgery device of the invention which is equipped with a high frequency generator that produces a purely sinusoidal output voltage $U_a$. In this circuit block diagram there is shown, in addition to the elements described with reference to FIG. 1, is a low pass filter 18 to which the output of the high frequency generator that consists of an oscillator 1, an amplifier and an output transformer 3 is supplied, so that the output terminals 10 and 11 receive only the fundamental frequency of the oscillator 1 from the output of the low-pass filter 18.

The automatic regulation of the output voltage $U_a$ in contrast to the heretofore known high frequency electro-surgery devices in which the output voltage is either insufficiently or not at all automatically regulated, have the advantage that the output voltage can be automatically monitored in simple and indicated on an electronic indicated. Since the level of the output voltage $U_a$ is an important parameter for surgical coagulation and/or cutting procedures, but it is important to be able to set this value before the beginning of the procedure since it now can be done with sufficient accuracy to lead to reproducible results.

Figure 3:
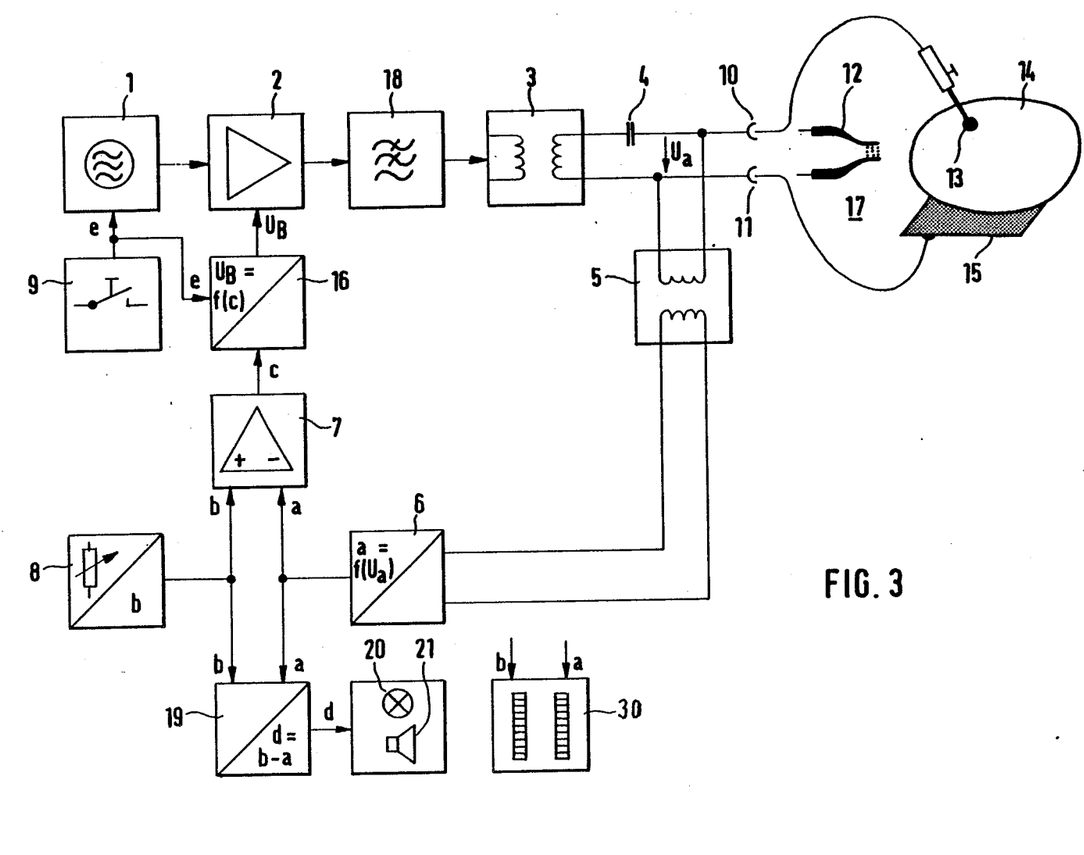
FIG. 3 is a circuit block diagram of an advantageous modification of high frequency electro-surgery apparatus according to the invention.

FIG. 3 shows a modification of the electro-surgery device schematically represented in FIG. 2 which is of interest in connection with the above remarks. The embodiment of FIG. 2 being again shown in circuit block diagram. Since the electrical signal $a = f(U_a)$ is proportional to the output voltage $U_a$, this signal can be compared in a simple way with the signal b which sets a desired value of $U_a$. If a differs from b, this deviation can be optically or acoustically signalized. Positive and/or negative deviations can be signalized at thresholds that can be set independently of each other and the user may choose whether either or both should set off optical and/or acoustic signals 20, 21.

In addition, the signal a and/or the signal b can be indicated by an electronic indicator device 30 for example by means of so-called bargraph indication 30.

Figure 4:
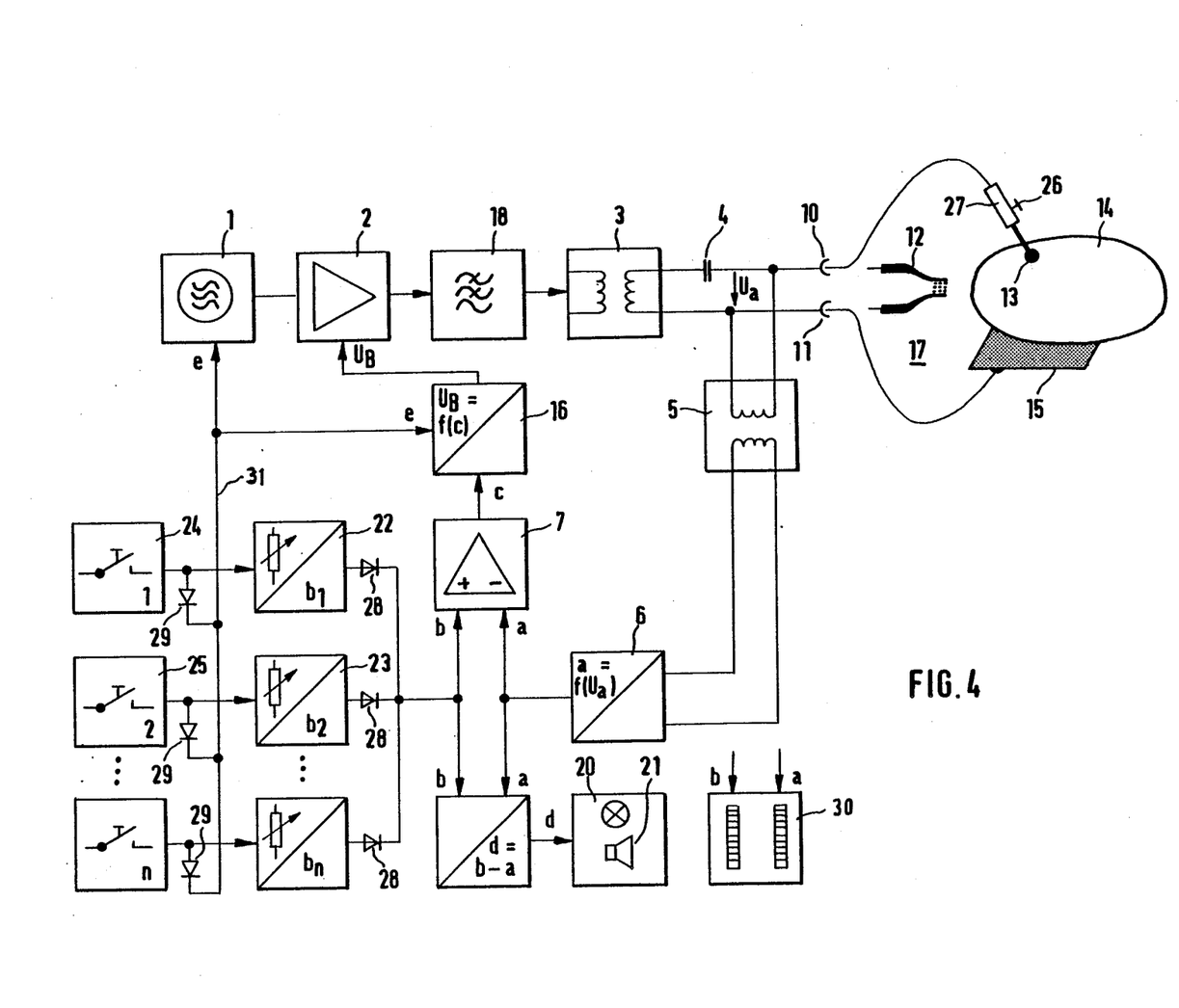
FIG. 4 is a circuit block diagram of a second advantageous modification of high frequency electro-surgery apparatus according to the invention.

FIG. 4 shows a further modification, in the above-described respects, of the embodiment described in FIG. 3, again shown in circuit block diagram form. This embodiment is provided with a number of reference voltage value sources 22, 23... n which are respectively subject to activation by separate keys on an electrode handle and/or by pedals 24, 25... n. Whereas in the previous illustrative embodiments respectively described in FIGS. 1, 2 and 3 a single reference voltage value source is provided to deliver continuously reference value signals b, in the case of a number of reference value sources as shown in FIG. 4, attention must be given to the fact that the particular selected reference voltage value should be delivered to the regulating amplifiers 7 only so long as the corresponding reference value source 22, 23... n remains in activation in response to operation of a key or pedal 24, 25... n. The respective reference value sources could, however, also be selected by keys or buttons on the front panel of the high frequency surgery device and then activated in each case by a single button 26 in the electrode handle 27 or by the single pedal switch. The outputs of the individual reference value sources are decoupled from each other by diodes 28. The activation signal e is produced with operation of any of the key switches 24, 25... n, the signals of which are diode coupled for oscillation reasons, the diodes 29 to an activation command bus 31. The activation signal e is supplied not only to the oscillator 1, but also to the electronically controlled power supply 16, so that this power supply delivers the operating voltage $U_b$ for the amplifier 2 only when 1 of the keys or pedals 24, 25... n is pressed.

In the case of all of the illustrated embodiments, attention should be given to the fact that at the instant at which the reference value signal b begins to take effect through the regulating amplifiers 7 on the amplifier 2 or on the electronically controlled power supply 16 while the signal a has not yet been applied to the regulating amplifier, it should not be possible for the output voltage $U_a$ to rise unacceptably above the desired reference value, even for a very brief interval of time. The extent to which that may happen depends upon the regulation time constant of the regulation loop. For this reason it is desirable, for example, that the electronically controlled power supply 16 should be so designed that the rate of rise of the operating voltage $U_b$ should not be too steep, but should be so determined by the regulation time constant of the regulation loop that the operating voltage $U_b$ of the amplifier 2 should rise at such a rate that $U_a$ at the momemt of switching on of the equipment should not rise to an unacceptable level as a result of delay in the regulation loop.

Although the invention has been described with reference to particular illustrative examples, it will be understood that variations and modifications are possible within the inventive concept.

I claim:

1. High frequency electro-surgery apparatus for cutting and/or coagulating biologic tissues comprising a high frequency AC generator having an oscillator (1), an amplifier (2), connected to said oscillator, an output transformer (3) connected to said amplifier and having an output winding, a series capacitor (4) connected to said output winding for blocking possible low frequency components of output, a pair of output terminals (10, 11) connected respectively to said series capacitor and said output winding and forming part of a utilization circuit (17), and utilization means including electrodes for application to a patient which are connectable to said output terminals, and further comprising:

electrically isolating and signal coupling means, having an input connected across said utilization circuit (17) on the output side of said blocking capacitor at locations selected for sensing high frequency AC output voltage of said electro-surgery apparatus and having an output coupled to but electrically isolated from said input;

voltage conversion means (6) connected to the output of said isolating and coupling means, and having an output, for supplying a variable DC voltage signal ($f(U_a)$) which is proportional to a measure of said high frequency AC voltage sensed at said input of said isolating and coupling means;

source (8) of an adjustable steady reference voltage (b) for setting a desired value of said measure of said high frequency AC voltage;

a regulating amplifier (7) having an input, a first input connected to said output of said voltage conversion means and a second input connected to said reference voltage source (8) for comparing voltages at its said inputs and supplying regulating control voltage at its said output;

an electronically controllable power supply (16) connected to said regulating amplifier for response to said control voltage and connected to said amplifier for energizing said amplifier and thereby varying the output of said amplifier (2) of said high frequency AC generator in accordance with said control voltage in a manner regulating said output DC voltage of said voltage conversion means to and at said desired value thereof set by said reference voltage source (8).

2. Electro-surgery apparatus as defined in claim 1, wherein said input of said isolating and coupling means is connected to said output terminals (10, 11).

3. Electro-surgery apparatus as defined in claim 1, wherein said electronically controllable power supply includes means for varying an electric power supply voltage ($U_b$) for said amplifier (2) of said high frequency AC generator.

4. Electro-surgery apparatus as defined in claim 3, wherein said power supply voltage varying means are included in a said electronically controllable power supply energized by commercially available and publicly distributed electric power.

5. High frequency electro-surgery device as defined in claim 3, wherein said means for varying said electric power supply voltage ($U_b$) for said amplifier (2) has a maximum rate of rise for said electric power supply voltage ($U_b$) that is determined with reference to the regulation time constant of a regulation loop in which said regulating amplifier (7) operates so that the rise of said electric power supply voltage ($U_b$), right after said apparatus is switched on, is such that said output high frequency AC voltage ($U_a$) will not rise to an unacceptable value as a result of delay in regulation.

6. Electro-surgery apparatus as defined in claim 1, wherein said isolating and coupling means include an isolating coupling device selected from the group consisting of isolating transformers and optocouplers.

7. Electro-surgery apparatus as defined in claim 1, wherein said utilization circuit includes a low-pass filter (18) interposed between said amplifier (2) and said output transformer (3) of said high frequency electro-surgery apparatus.

8. High frequency electro-surgery apparatus as defined in claim 1, wherein means are provided connected to said regulating amplifier which are responsive to the magnitude of the difference between the output of said voltage conversion means and said reference voltage for providing a visible signal (20) and/or an acoustic signal (21) whenever the magnitude of said difference (d) exceeds a predetermined tolerance limit for said difference.

9. High frequency electro-surgery apparatus as defined in claim 1, wherein indicating means (30) are provided for displaying the reference value of said measure of said output AC voltage ($U_a$) represented by the value of reference voltage the actual value of said measure of said output AC voltage ($U_a$), or both.

10. High frequency electro-surgery device as defined in claim 1, wherein additional reference value signal sources, independent of each other, are provided and also means for selecting, by switching a selected reference value signal source, said selecting means being provided by finger switches in a handle (27) of a said electrode, by pedals (24, 25... n) or by both finger switches and pedals.

11. High frequency electro-surgery device as defined in claim 1, wherein said measure of said output high frequency AC voltage ($U_a$) to which the output signal of said voltage conversion means is proportional is the peak value of said output high frequency AC voltage.

12. High frequency electro-surgery device as defined in claim 1, wherein said measure of said output high frequency AC voltage ($U_a$) to which the output signal of said voltage conversion means is proportional is the effective value of said output high frequency AC voltage.

13. High frequency electro-surgery device as defined in claim 1, wherein said measure of said output AC high frequency voltage ($U_a$) to which the output signal of said voltage conversion means is proportional is an average value of said output high frequency AC voltage.

14. High frequency electro-surgery device as defined in claim 1, wherein said isolating and coupling means include a glow lamp connected to its input and a circuit having a photoelectric component illuminated by said glow lamp which circuit is connected to its output.

15. High frequency electro-surgery apparatus for cutting and/or coagulating biologic tissues comprising a high frequency AC generator having an oscillator (1), an amplifier (2) connected to said oscillator, an output transformer (3) connected to said amplifier and having an output winding, a pair of output terminals (10, 11) connected to said output winding for supply of high frequency electric current to said terminals and forming part of a utilization circuit (17) and utilization means including electrodes for application to a patient which are connectable to said output terminals, and further comprising:

means, having an output and having an input connected across said utilization circuit at locations selected for sensing an actual value of the high frequency AC voltage ($U_a$) across said utilization circuit at said output terminals (10, 11), for producing a DC voltage signal proportional in voltage to said actual value of said high frequency AC voltage;

means, having an output, for generating a reference value voltage signal at said output;

voltage comparison means (19) having an output and having a first input connected to said output of said means for producing a DC voltage signal proportional to said actual value of said AC voltage and second input connected to said output of said reference value voltage signal generating means, and means connected to said output of said comparison means for generating an optical signal (20) and/or an acoustic signal (21) when predetermined tolerance limits for the difference (d) between said reference value voltage signal (b) and said DC voltage signal (a) are exceeded.

16. High frequency electro-frequency apparatus for cutting and/or coagulating biologic tissues comprising a high frequency AC generator having an oscillator (1), an amplifier (2) connected to said oscillator, an output transformer (3) connected to said amplifier and having an output winding, a pair of output terminals (10, 11) connected to said output winding and forming part of a utilization circuit (17) and utilization means including electrodes for application to a patient which are connectable to said output terminals and further comprising:

means, having an output and having an input connected across said utilization circuit at locations selected for sensing an actual value of high frequency AC voltage ($U_a$) across said utilization circuit, at said output terminals (10, 11), for producing, at said output, a DC voltage signal proportional in voltage to said actual value of said high frequency AC voltage;

means for generating a reference value of voltage and for comparing said reference value voltage with said DC voltage signal produced at said output of said means having an input connected across said utilization circuit, and display means connected to said reference value generating and voltage comparing means for providing a display representative of said reference value of voltage, said DC voltage signal proportional in voltage to said actual value of high frequency AC voltage ($U_a$), or both.

* * * * *